US008512760B2

(12) United States Patent
Cairns et al.

(10) Patent No.: US 8,512,760 B2
(45) Date of Patent: Aug. 20, 2013

(54) NANO-PARTICLE DISPERSIONS

(75) Inventors: James Anthony Cairns, Dundee (GB); Roderick Allan George Gibson, Dundee (GB); Graham James Berry, Dundee (GB)

(73) Assignee: The University Court of the University of Dundee (GB)

( * ) Notice: Subject to any disclaimer, the term of this patent is extended or adjusted under 35 U.S.C. 154(b) by 354 days.

(21) Appl. No.: 12/744,225

(22) PCT Filed: Nov. 21, 2008

(86) PCT No.: PCT/GB2008/003903
§ 371 (c)(1),
(2), (4) Date: Sep. 23, 2010

(87) PCT Pub. No.: WO2009/066079
PCT Pub. Date: May 28, 2009

(65) Prior Publication Data
US 2011/0027385 A1 Feb. 3, 2011

(30) Foreign Application Priority Data

Nov. 23, 2007 (GB) .................................. 0722989.1
Jan. 19, 2008 (GB) .................................. 0801013.4

(51) Int. Cl.
*A61K 9/10* (2006.01)
*A61K 9/14* (2006.01)
*A61K 31/28* (2006.01)
*A61K 31/74* (2006.01)
*A61K 33/24* (2006.01)

(52) U.S. Cl.
USPC ........ 424/604; 424/78.08; 424/489; 424/646; 514/492; 977/775; 977/776; 977/777; 977/810

(58) Field of Classification Search
None
See application file for complete search history.

(56) References Cited

U.S. PATENT DOCUMENTS

| | | | |
|---|---|---|---|
| 4,634,468 A | 1/1987 | Gulla et al. |
| 5,424,009 A | 6/1995 | Asrar |
| 5,698,483 A | 12/1997 | Ong et al. |
| 6,267,590 B1 | 7/2001 | Barry et al. |
| 6,462,095 B1 | 10/2002 | Bönsel et al. |
| 6,720,006 B2 | 4/2004 | Hanke et al. |
| 6,924,325 B2 | 8/2005 | Qian |
| 2007/0213460 A1 | 9/2007 | Ruppert et al. |

FOREIGN PATENT DOCUMENTS

| | | |
|---|---|---|
| DE | 19740431 C1 | 11/1998 |
| DE | 19740431 C1 | 11/1998 |
| EP | 0187962 | 7/1986 |
| EP | 0271466 | 6/1988 |
| EP | 1436445 | 7/2004 |
| GB | 1181794 | 2/1970 |
| JP | 8085807 | 4/1996 |
| WO | WO 2006/072959 | 7/2006 |

OTHER PUBLICATIONS

R. P. Pohanish and S. A. Green, Wiley Guide to Chemical Incompatibilities, John Wiley & Sons, Aug. 2009, p. 1096 (entry for zirconium nitrate).*
Noonan et al. "Structure and Chemical Sensing Applications of Zirconium Acetate Sol-Gel Films," Chem. Mater. 1995, 7, pp. 1117-1123.*
Sigma-Aldrich product description of Sigma-Aldrich's zirconium acetate solution in dilute acetic acid, accessed on Jan. 9, 2013 at http://www.sigmaaldirch.com/catalog/products/aldrich/413801?lang=en&region=US.*
Bradley et al. "Metal Oxide Alkoxide Polymers Part I. The Hydrolysis of Some Primary Alkoxides of Zirconium," Canadian Journal of Chemistry, Jul. 1961, vol. 39, No. 7, pp. 1434-1443.
Dunworth, et al. "Noble Metal-Synthetic Polymer Catalysts and Studies on the Mechanism of Their Action," Advanced Catalysis, 1954, vol. 6, pp. 125-141.
Kiwi et al. "Protection, Size Factors, and Reaction Dynamics of Colloidal Redox Catalysts Mediating Light Induced Hydrogen Evolution from Water," Journal of the American Chemical Society, Nov. 21, 1979, vol. 101, No. 24, pp. 7214-7217.
Mayer et al. "Poly(2-hydroxyalkyl methacrylates) as stabilizers for colloidal noble metal nanoparticles." Polymer, Feb. 2000, vol. 41, No. 4, pp. 1627-1631.
Panigrahi et al. "General method of synthesis for metal nanoparticles." Journal of Nanoparticle Research, Aug. 2004, vol. 6, No. 4, pp. 411-414.
Rampino et al. "Relationship Between Particle Size and Efficiency of Palladium-Polyvinyl Alcohol (Pd-PVA) Catalysts," Proceedings of the National Academy of Sciences of the U.S.A., Aug. 1943, vol. 29, No. 8, pp. 246-256.
Turkevich et al. "A Study of the Nucleation and Growth Processes in the Synthesis of Colloidal Gold," Discussions of the Faraday Society, 1951, vol. 11, pp. 55-75. Van Der Putten et al. "Electrochemistry of Colloidal Palladium an Experimental Study of Sol Formation and Electrocatalysis," Journal of Electrochemical Society, Dec. 1992, vol. 139, No. 12, pp. 3475-3480.
Ray et al. "Formation of Cr3+ stabilized ZrO2 nanocrystals in a single cubic metastable phase by a novel chemical route with a sucrose-polyvinyl alcohol polymer matrix," Materials Letters, Apr. 2001, vol. 48, No. 5, pp. 281-291.
Zielen et al. "The Hydrolytic Polymerization of Zirconium in Perchloric Acid Solutions," Methods, Nov. 20, 1956, vol. 78, No. 22, pp. 5785-5792.
Written Opinion for International (PCT) Patent Application No. PCT/GB2008/003903, mailed Jan. 7, 2010, 9 pages.

* cited by examiner

*Primary Examiner* — James H. Alstrum-Acevedo
(74) *Attorney, Agent, or Firm* — Sheridan Ross P.C.

(57) ABSTRACT

A process for the production of an aqueous dispersion of metal nano particles comprising palladium is provided. The process comprises the admixture of a water soluble organic polymer, a palladium salt and a first reducing agent to an aqueous liquid. The first reducing agent is a metal-containing polymer which has reducing properties or a saccharide which has reducing properties. The nano particles can include a second metal. The dispersions can be used as catalysts for electroless plating, to produce heterogeneous catalysts and in the production of anti-microbial devices and compositions.

18 Claims, 3 Drawing Sheets

_US 8,512,760 B2_

NANO-PARTICLE DISPERSIONS

CROSS REFERENCE TO RELATED APPLICATIONS

This application is a national stage application under 35 U.S.C. 371 of PCT Application No. PCT/GB2008/003903 having an international filing date of 21 Nov. 2008, which designated the United States, which PCT application claimed the benefit of Great Britain Application Nos. 0722989.1 filed 23 Nov. 2007 and 0801013.4 filed 19 Jan. 2008, the entire disclosure of each of which are hereby incorporated herein by reference.

FIELD OF THE INVENTION

The present invention relates to a novel process for creating stable dispersions of nano-particulate palladium and other metals in an aqueous medium and includes methods for their use in a number of different applications.

BACKGROUND TO THE INVENTION

Techniques for depositing metals on to surfaces are of great importance for many applications, including the fabrication of electronic devices. This has resulted in the evolution of several enabling techniques, of which electroless deposition is well-established. In this case the substrate is coated first with a catalytic layer. This is done conventionally by immersing the substrate in a solution containing a divalent tin ($Sn^{2+}$) salt, followed by immersion in a solution containing a palladium salt. The palladium ions are thereby reduced to metallic palladium in a redox reaction which involves the oxidation of $Sn^{2+}$ to $Sn^{4+}$. The substrate is subsequently washed to remove residual tin ions, then immersed in a specially formulated solution containing a salt of the metal to be deposited, together with a reducing agent, such as formaldehyde. The palladium catalytic sites on the surface of the substrate facilitate the reduction of the metal salt, causing a metallic film to be deposited on to the substrate.

The production of catalytic coatings prior to electroless plating has been the subject of a great deal of research activity in the past. Two of the objectives of previous inventions were: (1) how to activate the catalyst prior to electroless plating; and (2) how to ensure that the electroless plating bath does not become contaminated with the catalyst. The first of these objectives is discussed in EP0271466, in which the catalyst is associated with a polymeric species; and the relative merits of activating the resultant catalyst-containing coating with ultraviolet light and heat are disclosed. The second objective is addressed in U.S. Pat. No. 5,424,009, and describes also the advantages of associating the catalytic salt with a polymeric species to prevent contamination of the plating bath with the catalyst. In both cases it is necessary to activate the catalyst prior to immersing it in the electroless plating bath.

It was recognised in European patent number EP1436445 that the electroless deposition process could be improved substantially if the catalyst was applied to the substrate as a thin film, in which the catalyst was dispersed within a porous ceramic-type matrix. There are several advantages associated with this approach. For example, the catalyst can be activated simply by heating; while the porous ceramic-type matrix can be selected to achieve strong adhesion to the substrate. The result is that when the electroless deposition process is applied to the coated substrate, the deposited metal builds up from the catalytic nuclei located within the porous matrix, thereby producing a metal film which is strongly bonded to the substrate. In this process organic precursors of both the ceramic-type matrix and the catalytic particles were applied to the substrate as a coating, then heated to convert it to an active catalyst, suitable for subsequent electroless deposition. In EP1436445 an example is described in which this heating step is conducted at 350° C., in order to achieve the objective of a strongly bonded copper film onto a glass substrate. This process works well for heat-resistant substrates, including glasses and ceramics, but it is inappropriate for substrates such as epoxy resins or certain types of plastic films, which can be damaged by exposure to the temperatures required to activate the catalyst and to form the ceramic coating.

DESCRIPTION OF THE INVENTION

It is an object of the present invention to provide dispersions of nano particles that can be used to provide catalytic coatings for electroless deposition and that have several other useful applications.

Thus according to a first aspect the present invention provides a process for the production of an aqueous dispersion of metal nano particles comprising palladium, the process comprising: the admixture of a water soluble organic polymer, a palladium salt and a first reducing agent selected from the group consisting of:
  i) a metal-containing polymer which has reducing properties; and
  ii) a saccharide which has reducing properties;
    to an aqueous liquid.

The process involves the admixture of various components to the aqueous liquid. It will be understood that the term admixture means that the components can be added simultaneously or sequentially in a selected order to the aqueous dispersion. Examples of sequential additions are given hereafter in the description of some preferred embodiments.

Preferably the palladium salt is selected from the group consisting of palladium nitrate or palladium chloride. Other palladium salts may be employed. The metal particulates produced in experiments described hereafter were typically of 3 nanometers particle size, as revealed by transmission electron microscopy, but other size particles may be produced by varying the conditions if desired, provided the particles produced are sufficiently small to remain dispersed in the selected aqueous medium.

The water-soluble polymer may be polyvinyl alcohol, polyvinyl acetate, starch or gelatine. Other water-soluble polymers may be employed. The water-soluble polymer may typically have a solubility in water of at least 1 g/liter.

Preferably the aqueous liquid is water. The aqueous liquid may contain other components if desired or required for a particular application.

Preferably the first reducing agent is selected from the group consisting of metal containing polymers, and saccharides. The reducing agents act to reduce the palladium salt to palladium metal.

The term reducing agent used throughout this description of the invention includes both conventional reducing agents such as, for example, hydrogen gas but also other agents that, when in combination with the water soluble polymer, act to reduce the metal salt.

Preferably where the first reducing agent is a metal containing polymer, it is selected from the group consisting of zirconium and hafnium containing polymers. More preferably the first reducing agent is selected from the group consisting of zirconium nitrate polymer and zirconium acetate polymer. These metal containing polymers have been found to act, in the presence of the water soluble polymer, as reducing agents for palladium salts i.e. there is a synergistic interaction between the metal containing polymer and the water soluble organic polymer, resulting in reduction of the palladium salt.

Use of a metal containing polymer in the dispersions has been found to provide a number of significant advantages. The metal containing polymer not only acts to reduce the palladium salt to the metal but it also facilitates the use of the dispersions in forming stable catalytically active coatings on a wide range of substrates as discussed hereafter. For example a zirconium/nitrate polymer can be employed. Such materials consist of zirconium-containing units, in association with nitrate ligands and are available from AMR Ltd. Its preparation is described in UK Patent Number 1,181,794, which states that: 'It would appear to be a large cationic polymer containing equimolar amounts of nitrate and zirconium in which the tetrameric units are joined by nitrato and diol bridges. If these are equal in number the compound can be written:—

$$[Zr_4(OH)_{12}(NO_3)_2(H_2O)_4]_n(NO_3)_{2n}.2NH_2O'.$$

Surprisingly if palladium nitrate is dissolved in an aqueous solution containing zirconium (nitrate) polymer (supplied by AMR Ltd.) and a water-soluble organic polymer, such as polyvinyl alcohol, then the palladium salt begins to decompose spontaneously, over a period of a few hours, to produce a dark-coloured liquid. It was found that the change in colour was due to the reduction of the palladium salt. This was confirmed by passing hydrogen-containing gas through a freshly prepared solution. In this case the solution darkened within a few minutes. Transmission electron microscopy confirmed that the palladium particle size was typically 3 nanometers. Thus metal containing polymers can be used in the process of the invention. Other reducing agents that can be employed are saccharides.

Preferably the saccharide is a disaccharide. More preferably the disaccharide is sucrose.

The process may further comprise the additional step of adding a salt of a second metal to the aqueous liquid after formation of the metal nano particles comprising palladium. This produces stable dispersions of metal nano particles, which comprise palladium and the second metal. It is believed that the palladium particles act as nuclei for the deposition of the second metal. The second metal may be selected from the platinum group metals or noble metals. Preferably the second metal is selected from the group consisting of platinum, rhodium, silver, gold and copper.

Preferably the process further comprises addition of a second reducing agent to the aqueous liquid. The second reducing agent may be selected from the group consisting of hydrogen gas and water-soluble reducing agents, for example sucrose or ascorbic acid. More preferably the second reducing agent is ascorbic acid.

Surprisingly the addition of a saccharide, for example fructose, glucose or sucrose, as part of the process has been found to improve the stability of dispersions of the invention, as well as providing a reducing effect.

The process of the invention produces stable dispersions of nano particles comprising palladium. Thus according to a second aspect the present invention provides an aqueous dispersion of nano particles comprising palladium metal suspended in an aqueous liquid comprising a water soluble polymer, and a metal containing polymer with reducing properties or a saccharide with reducing properties.

The dispersions can be used in a wide variety of applications to produce a number of different products. For example they may be used in the preparation of heterogeneous catalysts. Heterogeneous catalysts are prepared conventionally by impregnating a ceramic support material with a solution containing a salt of the catalytic metal. The catalyst salt is then reduced to the metal in situ. It is desirable to optimize the efficiency of the catalyst by producing it in the form of small, uniform metal particle clusters. This is important in applications such as fuel cells, in which the cost of the noble metal catalyst has an important influence on the overall financial viability of the device. However it is difficult in practice to ensure that all of the metal sites meet this requirement. In other applications the metal clusters may migrate over the surface of the support, thereby forming larger clusters and thus reducing the efficiency of the catalyst. This is likely to occur if the catalyst is operated in a high-temperature environment, such as occurs in vehicle exhaust emission control. Therefore there is a need for a process, which enables the catalyst to be synthesized as small particles in the presence of the support material, to which they are strongly bonded, or in which they are incorporated. The synthesis of catalytic nano-size metal particles as described in the present invention offers the opportunity to achieve this objective.

The dispersions of the invention are particularly suited to coating a surface with a catalytically active coating. Thus according to a third aspect the present invention provides a method of providing a surface with a catalytically active coating comprising the steps of:

preparation of an aqueous dispersion of palladium metal nano particles comprising: admixture of a water soluble organic polymer, a palladium salt and a first reducing agent for the palladium salt (as described before); to an aqueous liquid; and coating the surface with the aqueous dispersion of palladium metal nano particles.

For many applications the preferred first reducing agent is a metal containing polymer as discussed above and the method further comprises the step of drying the coating at temperatures typically between 30 and 150° C. Dispersions of the invention including a metal containing polymer, for example a zirconium polymer, can be applied to a large variety of surfaces to provide a catalytically active surface on which, for example electroless plating may be carried out. The dispersion can be applied to a large variety of substrates, including glass, plastic and epoxy resins, to produce uniform coatings. These coatings have been shown to be highly active for catalyzing the deposition of metal by electroless plating. In this case the coatings do not require a high temperature activation treatment. They require simply to be dried, at temperatures ranging from 30 to 150° C. The result is that the process is applicable to a much wider range of substrates, including those which were incapable of withstanding the temperatures required for processes such as those described in EP1436445.

After drying (for example at 105° C.) the coating becomes substantially insoluble in water. This is despite the temperature being much too low to cause, for example, the zirconium polymer to decompose to zirconium oxide. Thermo-gravimetric analysis (performed by AMR Ltd) has shown that decomposition to zirconium oxide requires heating to approximately 500° C. However such coatings, although formed at modest temperatures, are capable of withstanding, if necessary, much higher temperatures because the metal containing polymer component endows them with excellent thermal durability. For example, it was found that coatings made using zirconium nitrate polymer applied to high-temperature-resistant substrates can be heated to 800° C. without adversely affecting their subsequent performance for electroless plating. At this temperature the zirconium (nitrate) polymer will have decomposed to $ZrO_2$, as noted above.

The coatings also exhibit long-term stability. Thus coated specimens can be left at ambient (room temperature) conditions for long periods (several months) prior to electroless plating, without any apparent loss of catalytic activity.

Preferred substrates for coating by the methods of the invention include glass, ceramics, plastics, especially thermoplastics of low melting point, and cloth.

The aqueous dispersions of the invention can be conveniently applied by using a printing process, for example a contact printing or an inkjet printing process. Such methods allow the precise deposition of a catalytically active coating on a substrate. Naturally in these cases the physical properties of the ink would require to be optimized (for example in terms of its viscosity) so as to meet the requirements of the particular printing process. Having been deposited in this way, the ink can then, if desired, be subjected to electroless plating in order to build up a pattern in an appropriate metal, such as copper, nickel, or silver. Such methods can be used in a wide range of applications.

According to a fourth aspect the invention provides a process for plating a surface with a metal coating comprising the steps of:
preparation of an aqueous dispersion of palladium metal particles comprising: the admixture of a water soluble organic polymer, a palladium salt and a first reducing agent for the palladium salt (as described before); to an aqueous liquid; and
coating the surface with the aqueous dispersion of palladium metal particles to form a catalytically active coating;
drying the coating thus produced; and
carrying out an electroless plating process on the surface.

Advantageously the substrate, whose surface is plated in the process, may be chosen or modified to allow the coating and its constituent catalytically active nano particles to impregnate at least the near surface structure. The electroless plating process then provides a metal plating that is more strongly adhered to the substrate.

Preferably the electroless plating process is carried out with a metal salt selected from the group consisting of nickel, copper and silver salts. As discussed above the coatings of the invention can be applied precisely by using printing techniques, enabling the precise positioning and shaping of a pattern of electroless plated portions on a surface as required. An alternative method is to make use of photoresists as in conventional printed circuit manufacture. Thus the process for plating a surface with a metal may further comprise the steps of:
applying a photoresist to the electroless plated surface;
exposing portions of the photoresist to light;
removing unexposed photoresist to reveal selected portions of the plated surface;
electroplating the revealed portions of the plated surface to thicken the metal coating at the selected portions;
removing the developed photoresist; and
etching the metal coating for a short period so as to remove the metal coating from the surface where no electroplating has occurred, thereby providing a discontinuous metal coating on the surface. This process has advantages in the manufacture of printed circuit boards in comparison with conventional electroplating, as discussed hereafter.

Other uses of the dispersions of the invention include the manufacture of devices, which contain a dispersion of nano particles comprising palladium and silver. Silver is well known to have anti-microbial properties, especially when finely dispersed. Thus according to a fifth aspect the present invention provides an anti-microbial device or composition comprising a dispersion of nano particles comprising palladium and silver metal. The dispersion is prepared according to the process described above using a silver salt added after the formation of palladium particles to produce the desired silver containing nano particles. The anti-microbial devices or compositions may be, for example wound dressings, clothing, filters, cloth, ointment or paint.

The dispersions of the invention are particularly suited to providing catalysts, such as the heterogeneous catalysts discussed above. Mixed metal catalyst systems, with selected proportions of different metals, can be readily prepared as required by simply mixing aqueous dispersions with different metal content. The resulting mixture can then be processed as required to produce the desired catalyst, for example a heterogeneous catalyst of metal particles on a ceramic substrate.

BRIEF DESCRIPTION OF THE DRAWINGS

Further preferred features and advantages of the present invention will appear from the following detailed description of some embodiments illustrated with reference to the accompanying drawings in which.

DESCRIPTION OF SOME PREFERRED EMBODIMENTS AND EXPERIMENTAL RESULTS

Example 1

Dispersions Containing Zirconium Polymer

Figure 1:
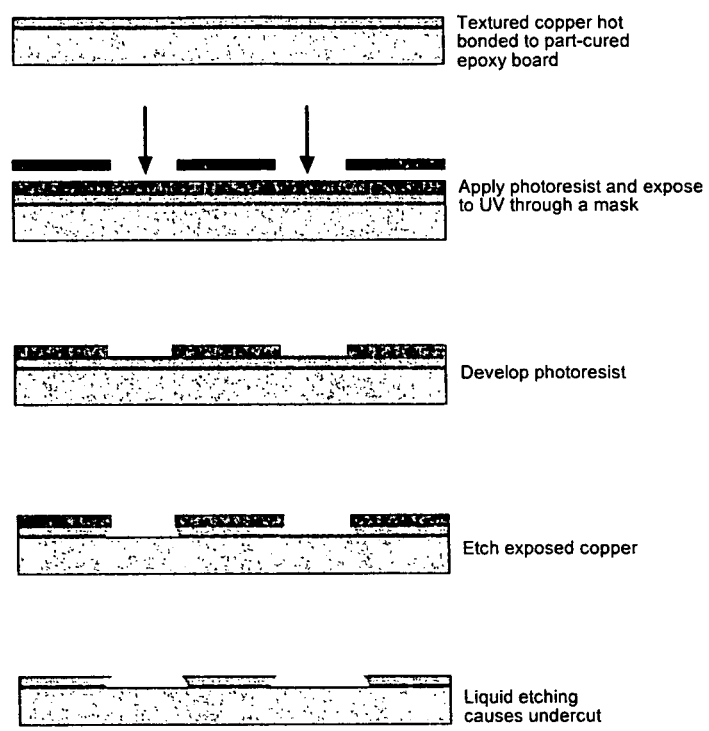
FIG. 1 shows a prior art method for producing metal tracks.

Palladium nitrate was dissolved in an aqueous solution containing zirconium (nitrate) polymer (supplied by AMR Ltd.) and a water-soluble organic polymer, polyvinyl alcohol. The palladium salt began to decompose spontaneously, over a period of a few hours, to produce a dark-coloured liquid. It was found that the change in colour was due to the reduction of the palladium salt. It was observed in these experiments that it was necessary to have a carefully optimized ratio of palladium salt; zirconium polymer; and water-soluble polymer in order to produce a stable, catalytically active dispersion. Deviations from this ratio can result in an unstable liquid, from which the palladium slowly settles out; or in a poorly performing catalyst. However, such dispersions can be stable and usable over a short period of several days or more. Table 1 shows how variations in the composition of the liquid can cause significant changes in the stability of the metal dispersion and also on the abilities of coatings derived from the liquids to achieve efficient electroless deposition (the latter measured using Rohm and Haas Niposit® 468 nickel plating solution).

TABLE 1

The influence of variations in the ratios of PVA (polyvinyl alcohol); zirconium (nitrate) polymer (equivalent $ZrO_2$ concentration); and palladium nitrate on the stability of the metal dispersions and on the performances of the coatings produced from these liquids in achieving Ni electroless deposition

| Components | | | Metal dispersion | Ni electroless |
|---|---|---|---|---|
| PVA (g/l) | $ZrO_2$ (g/l) | $Pd(NO_3)_2$ (g/l) | stability (over 3 weeks) | deposition (Relative Rates) |
| 10 | 13 | 2.50 | Unstable | Fast |
| 5 | 6.5 | 1.25 | Stable | Medium |
| 5 | 6.5 | 2.50 | Some settling | Fast |
| 5 | 52 | 5.00 | Unstable (<1 day) | Very fast |
| 20 | 13 | 2.50 | Stable | Slow |
| 5 | 26 | 2.50 | Unstable | Slow |
| 5 | 13 | 2.50 | Unstable | Fast |
| 5 | 6.5 | 1.25 | Unstable | Fast |

In addition, the choice of the palladium salt is an important factor. For example it was observed that palladium nitrate was superior to palladium chloride in achieving spontaneous reduction of the palladium salt. Palladium chloride requires an additional reducing agent (for example hydrogen) in order to achieve reduction to palladium. It was noted also that all three of the components had to be present for spontaneous reduction to take place. Thus palladium nitrate dissolved in a solution containing only zirconium (nitrate) polymer, or palladium nitrate dissolved in a solution containing only polyvinyl alcohol shows little or no tendency to produce metallic palladium spontaneously at room temperature. However if hydrogen is bubbled through these solutions, the palladium nitrate/polyvinyl alcohol quickly darkens to form a uniform dispersion, whereas the palladium nitrate/zirconium (nitrate) polymer solution darkens only slowly, and rather than forming a uniform dispersion, the palladium precipitates out from the solution. This suggests that the palladium becomes preferentially associated with the polyvinyl alcohol in forming a stable dispersion.

Example 2

Preparation of a Nanoparticulate Palladium Containing Dispersion

We now describe the preparation of the most stable dispersion shown in Table 1 (second row). A solution of polyvinyl alcohol of molecular weight 85,000 to 146,000 (Sigma-Aldrich Co.) was prepared using deionised water. To this was added a solution of zirconium (nitrate) polymer, followed by ultrasonic agitation for approximately 15 min. An aqueous palladium nitrate solution was then added, followed once more by ultrasonic agitation for 15 min and then allowed to stand at room temperature. The concentration of the components was: polyvinyl alcohol: 5 g/l; zirconium (nitrate) polymer (expressed as $ZrO_2$ content): 6.5 g/l; and palladium nitrate: 1.25 g/l. After approximately one hour the solution was observed to darken, and after 48 hours it had become completely black. Alternatively, this result can be achieved in a few minutes by passing hydrogen-containing gas (5% hydrogen in nitrogen) through the liquid. Transmission electron microscopy revealed that the solution contained palladium particulates having a mean diameter of 3 nanometers. The water-soluble organic polymer used in this preparation (polyvinyl alcohol) is generally preferred, and therefore is used in the subsequent examples detailed below. However other water-soluble polymers, such as polyvinyl acetate, may be used in specific applications.

Example 3

The Beneficial Effects of Sucrose on Nano-Particulate Metallic Dispersions

The palladium nano-particulate-containing dispersion described above in Example 2 was more stable than the other variants described in Table 1. However it was observed that over a period of several weeks at room temperature it showed a tendency to settle out, although it was found that this behaviour could be substantially slowed down by storing the liquid in a refrigerator (at typically 4° C.). We then discovered that if sucrose was incorporated into the liquid along with the water-soluble organic polymer, and before the addition of the palladium nitrate, the resultant nano-dispersion of palladium remained stable at room temperature, and showed no tendency to settle out even after several months. In addition, it was found that the preparation of the dispersion could, if required, be achieved rapidly by using a water-soluble reducing agent, of which ascorbic acid was effective. This new approach is described by way of examples detailed below.

Example 4

Improved Method for Producing Nano-Particulate Palladium Dispersions (a) An aqueous solution was prepared by adding consecutively: polyvinyl alcohol (5 g/l); sucrose (10 g/l); zirconium (nitrate) polymer (6.5 g/l equivalent $ZrO_2$ concentration); and palladium nitrate (1.25 g/l). The solution slowly darkened at room temperature over the following two days, to produce a black, stable palladium nano dispersion. The incorporation of sucrose caused the dispersion to remain stable, with no tendency to settle out, even after several months at ambient temperature. Hence the sucrose has imparted a further improvement in stability to the most stable dispersion shown in Table 1 (second row). A further proof of the remarkable stabilising influence of sucrose was then demonstrated by using one of the dispersions in Table 1 (first row) which had been found to be relatively unstable. For this purpose an aqueous solution was prepared by adding consecutively: polyvinyl alcohol (10 g/l); sucrose (10 g/l); zirconium (nitrate) polymer (13 g/l equivalent $ZrO_2$ concentration); and palladium nitrate (2.5 g/l). The solution slowly darkened at room temperature over the following two days, to produce a black, stable palladium nano-dispersion. The stability of the palladium nano-dispersion may be increased in some embodiments by the use of higher concentrations of sucrose for example at 20 g/l.

(b) An aqueous solution was prepared by adding consecutively: polyvinyl alcohol (5 g/l); sucrose (10 g/l); zirconium (nitrate) polymer (6.5 g/l equivalent $ZrO_2$ concentration); and palladium nitrate (1.25 g/l). To this was added ascorbic acid (0.1 g/l). This caused the rapid production of a black stable palladium nano-dispersion.

(c) An aqueous solution was prepared by adding consecutively: polyvinyl alcohol (5 g/l); sucrose (10 g/l); and palladium nitrate (1.25 g/l). To this was added ascorbic acid (0.1 g/l). This caused the rapid production of a black, stable palladium nano dispersion.

(d) An aqueous solution was prepared by adding consecutively: polyvinyl alcohol (5 g/l); sucrose (10 g/l); and palladium nitrate (1.25 g/l), and left to stand at room temperature.

It was observed that this solution began to darken in colour. Over the next 24 hours it became transformed to a black, stable palladium nano-dispersion. A corresponding solution containing only polyvinyl alcohol and palladium nitrate in the same concentrations showed no tendency to produce a palladium nano-dispersion over the same timescale. Therefore it can be concluded that the sucrose has behaved as a mild reducing agent.

(e) An aqueous solution was prepared by adding consecutively sucrose (10 g/l) and palladium nitrate (1.25 g/l), and left to stand at room temperature for 24 hours. It was then observed that a black granular precipitate of palladium had settled out from the solution. This proves that sucrose has acted as a reducing agent, as concluded from (d) above, and also illustrates the beneficial influence of polyvinyl alcohol in the creation of a stable palladium nano-dispersion.

(f) An aqueous solution was prepared by adding consecutively: zirconium (nitrate) polymer (6.5 g/l equivalent $ZrO_2$ concentration); sucrose (10 g/l); and palladium nitrate (1.25 g/l) and left to stand at room temperature for 24 hours. A black granular precipitate of palladium was observed to settle out from the solution. Hence once more, as concluded from (d) and (e) above, the presence of polyvinyl alcohol is required to maintain a stable nano-dispersion of palladium.

(g) An aqueous solution was prepared by adding consecutively: zirconium (nitrate) polymer (6.5 g/l equivalent $ZrO_2$ concentration); sucrose (10 g/l); and palladium nitrate (1.25 g/l). To this was added ascorbic acid (0.1 g/l). A black granular precipitate of palladium was observed to settle out rapidly from the solution. Once more, this shows that the presence of polyvinyl alcohol is required to achieve a stable nano-dispersion of palladium.

Example 5

Preparation of Stable Nano-Particulate Dispersions of Platinum, Rhodium, Silver, Gold and Copper We have discovered that stable nano-particulate dispersions of several metals can be produced in a novel manner by making use of nano-particulate dispersions of palladium. For this purpose, two palladium nano-dispersions were prepared as follows.

(Pd/1) An aqueous solution was prepared by adding consecutively: polyvinyl alcohol (5 g/l); sucrose (10 g/l); and zirconium (nitrate) polymer (6.5 g/l equivalent $ZrO_2$ concentration), followed by ultrasonic agitation in a water bath at typically 50° C. for 15 minutes. To this was added palladium nitrate to a concentration of 0.125 g/l, followed once more by ultrasonic agitation for 15 minutes in a water bath at typically 50° C. The resultant solution slowly darkened to produce a black, stable palladium nano-dispersion.

(Pd/2) An aqueous solution was prepared by adding consecutively: polyvinyl alcohol (5 g/l); and sucrose (10 g/l), followed by ultrasonic agitation for 15 minutes in a water bath at typically 50° C. To this was added palladium nitrate to a concentration of 0.125 g/l, followed once more by ultrasonic agitation for 15 minutes in a water bath at typically 50° C. The resultant solution slowly darkened to produce a black, stable palladium nano-dispersion.

Platinum

Attempts were made initially to prepare platinum dispersions, using a similar approach to that used to produce palladium nano-dispersions Thus an aqueous solution was prepared by adding consecutively: polyvinyl alcohol (5 g/l); sucrose (10 g/l); zirconium (nitrate) polymer (6.5 g/l equivalent $ZrO_2$ concentration); and potassium tetrachloroplatinate [$K_2PtCl_4$] (2.25 g/l). Ascorbic acid (1 g/l) was then added. This caused the fairly rapid production of a dark platinum dispersion. However over the following several days this dispersion showed a gradual tendency to settle out at room temperature. It should be noted that in the absence of ascorbic acid there was no evidence of the platinum salt spontaneously reducing to produce a platinum dispersion.

It was then discovered that the objective of producing stable nano-dispersions of platinum could be achieved by making use of palladium nano-dispersions. Two examples of this approach are described below.

(a) A black, stable palladium nano-dispersion was prepared, as described above under '(Pd/1)'. To this dispersion was added potassium tetrachloroplatinate (2.25 g/l), followed by ascorbic acid (1 g/l). This produced a black, stable nano-dispersion of platinum/palladium. Hence in this case the palladium has had the remarkable effect of producing a platinum-containing nano-dispersion, which showed effectively no tendency to settle out at room temperature.

(b) A black, stable palladium nano-dispersion was prepared, as described above under '(Pd/2)'. To this dispersion was added potassium tetrachloroplatinate (2.25 g/l), followed by ascorbic acid (1 g/l). This produced a black, stable nano-dispersion of platinum/palladium. Once more the palladium has played a vital role in the production of a stable platinum-containing nano-dispersion, which showed effectively no tendency to settle out at room temperature.

Rhodium (a) An aqueous solution was prepared by adding consecutively: polyvinyl alcohol (5 g/l); sucrose (10 g/l); zirconium (nitrate) polymer (6.5 g/l equivalent $ZrO_2$ concentration); and rhodium trichloride hydrate [$RhCl_3.xH_2O$] (1.125 g/l). To this was added ascorbic acid (1 g/l). No change in colour was observed. However when heated to 90° C. for one hour a dark rhodium dispersion was produced. This dispersion showed a tendency to settle out slowly.

(b) A black, stable palladium nano-dispersion was prepared, as described above under '(Pd/1)'. To this dispersion was added rhodium trichloride hydrate (1.125 g/l), followed by ascorbic acid (1 g/l). The liquid remained unchanged in appearance after heating at 90° C. for one hour. Since we know from (a) above that this heating procedure produces a rhodium nano-dispersion, we can be sure that the solution produced in this case now contains a stable nano-dispersion of rhodium /palladium.

(c) A black, stable palladium nano-dispersion was prepared, as described above under '(Pd/2)'. To this dispersion was added rhodium trichloride hydrate (1.125 g/l), followed by ascorbic acid (1 g/l). Once more, the liquid remained unchanged in appearance after heating at 90° C. Hence we see that, as in the case of platinum described above, the presence of palladium plays a significant role in producing a stable rhodium-containing nano-dispersion.

Silver (a) An aqueous solution was prepared by adding consecutively: polyvinyl alcohol (5 g/l); sucrose (10 g/l); zirconium (nitrate) polymer (6.5 g/l equivalent $ZrO_2$ concentration); and silver nitrate (2.75 g/l). To this solution was added ascorbic acid (0.5 g/l). This caused the production of a pale-coloured granular precipitate.

(b) A black, stable palladium nano-dispersion was prepared, as described above under '(Pd/1)'. To this dispersion was added silver nitrate (2.75 g/l), followed by ascorbic acid (0.5 g/l). This produced a stable nano-dispersion of silver/palladium.

(c) A black, stable palladium nano-dispersion was prepared, as described above under '(Pd/2)'. To this dispersion was added silver nitrate (2.75 g/l), followed by ascorbic acid (0.5 g/l). This produced a stable nano dispersion of silver/palladium.

Once more we see that, as in the case of platinum and rhodium, the presence of palladium plays a significant role in producing a stable silver-containing nano-dispersion.

Gold (a) An aqueous solution was prepared by adding consecutively: polyvinyl alcohol (5 g/l); sucrose (10 g/l); zirconium (nitrate) polymer (6.5 g/l equivalent $ZrO_2$ concentration); and potassium tetrachloroaurate ($K_2AuCl_4$) (2.25 g/l). To this solution was added ascorbic acid (1g/l). This caused the production of a reddish-purple dispersion, which settled out after a few days.

(b) A black, stable palladium nano-dispersion was prepared, as described above under '(Pd/1)'. To this dispersion was added potassium tetrachloroaurate (2.25 g/l), followed by ascorbic acid (1 g/l). This produced a reddish-purple, stable nano-dispersion of gold/palladium. Hence in this case the palladium has had the remarkable effect of producing a gold-containing nano-dispersion, which showed effectively no tendency to settle out at room temperature.

(c) A black, stable palladium nano-dispersion was prepared, as described above under '(Pd/2)'. To this dispersion was added potassium tetrachloroaurate (2.25 g/l), followed by ascorbic acid (1 g/l). This produced a reddish-purple, stable nano-dispersion of gold/palladium. Once more the palladium has played a vital role in the production of a stable gold-containing nano-dispersion, which showed effectively no tendency to settle out at room temperature.

Copper (a) An aqueous solution was prepared by adding consecutively: polyvinyl alcohol (5 g/l); sucrose (10 g/l); zirconium (nitrate) polymer (6.5 g/l equivalent $ZrO_2$ concentration); and copper (II) nitrate [$Cu(NO_3)_2$] (80 g/l). To this solution was added ascorbic acid (5 g/l). This caused the solution to change in colour from blue to green, indicating a reduction from Cu(II) to Cu(I). When the solution was then heated at 90° C. for 1 hour, a copper-coloured precipitate was produced, which was observed to oxidise to black copper oxide in a few hours.

(b) A black, stable nano-dispersion of palladium was prepared, as described above under '(Pd/1)'. To this was added copper (II) nitrate [$Cu(NO_3)_2$] (80 g/l), followed by ascorbic acid (5 g/l). This solution remained unchanged in appearance after heating at 90° C. for one hour. Since we know from (a) above that this heating process causes the production of copper oxide, we can conclude that the solution produced in this case now contains a stable nano dispersion of copper oxide/palladium.

(c) A black, stable nanodispersion of palladium was prepared, as described above under '(Pd/2)'. To this was added copper (II) nitrate [$Cu(NO_3)_2$] (80 g/l), followed by ascorbic acid (5 g/l). This solution remained unchanged in appearance after subsequent heating at 90° C. for one hour. Since we know from (a) above that this heating process causes the production of copper oxide, we can conclude that the solution produced in this case now contains a stable nano dispersion of copper oxide/palladium.

If desired, a copper metal containing nano dispersion may be prepared by a similar process to that of (b) or (c) above but carried out under an inert atmosphere. Such dispersions have a yellowish appearance.

Therefore once more, as in the case of platinum, rhodium and silver, the presence of the palladium plays a significant role in producing stable copper-containing nano-dispersions.

Confirmation of the Nano-Particulate Nature of the Metal Dispersions

Figure 3:
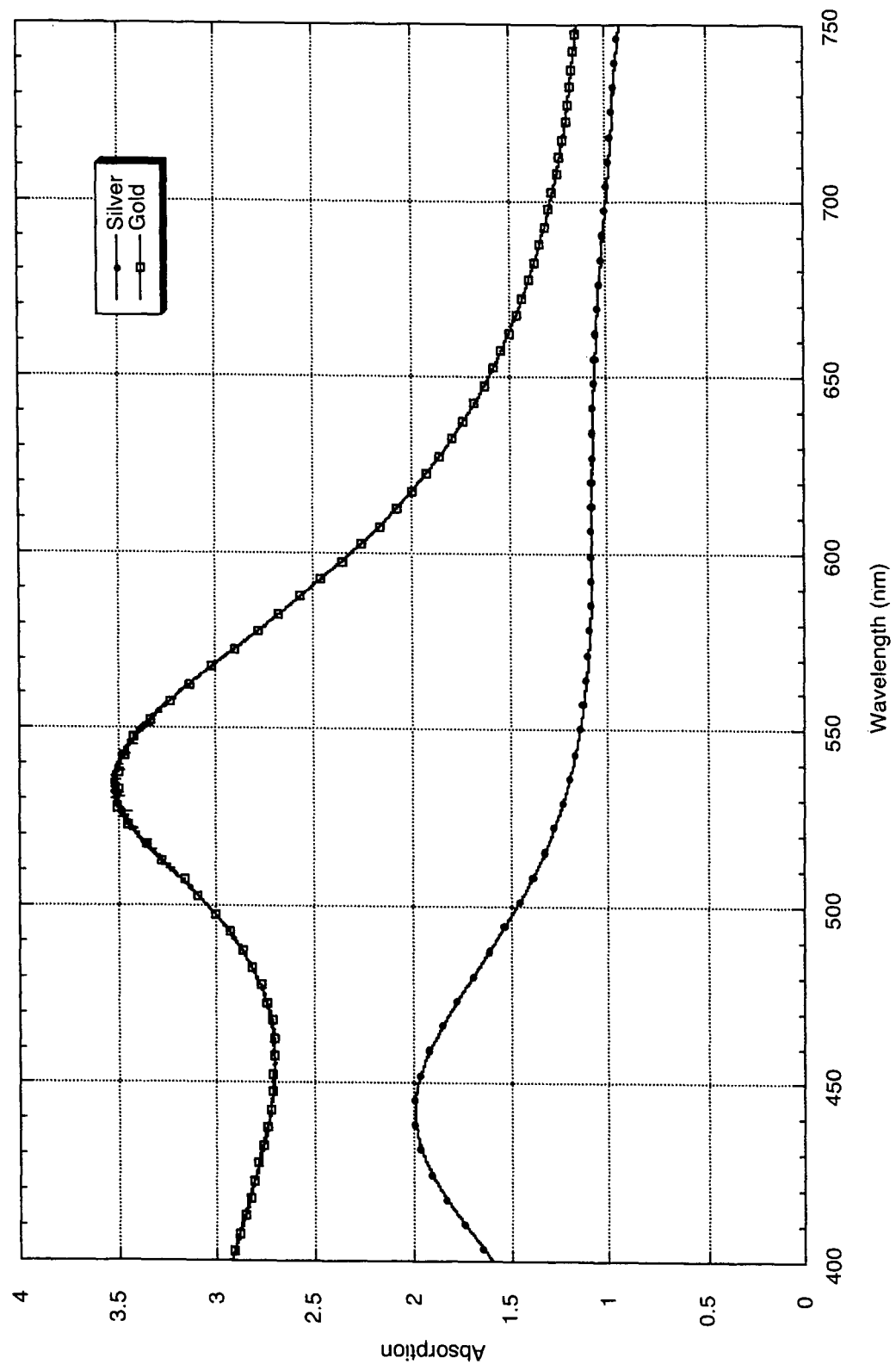
FIG. 3 shows optical absorption spectra of gold and silver nanoparticulate dispersions.

It has been observed that the metal dispersions produced as described above exhibit characteristic colours. For example the platinum dispersions are intensely black, the gold dispersions appear reddish-purple and the silver dispersions display a deep yellow hue. The reason for this is due to the phenomenon of surface plasmon resonance, which occurs when nano-dispersed metal interacts with incoming light, leading to preferential absorption at specific wavelengths. This is illustrated in FIG. 3, in which gold and silver are seen to exhibit absorption bands at the specific wavelengths within the visible spectrum expected for those metals in finely divided form. This thereby accounts for their observed colours, and confirms their nanoparticulate nature.

Incorporation of a High Surface Area Component into Metal Nanodispersions

It may be desirable in certain circumstances (such as the production of a heterogeneous catalyst) to disperse the metal nanoparticles more effectively by associating them with a high surface area material, such as a ceramic sol. In this way the availability of the metal particles for subsequent chemical reaction can be enhanced. We illustrate this by means of a typical example.

Example 6

Production of a Silver Nanodispersion Associated with a High Surface Area Ceramic Component Silver nitrate (16.5 g/l) is dissolved in a quantity of Pd/1. This in turn is added to an aqueous solution of ascorbic acid (3.5 g/l) containing a zirconia sol (35 g/l), in the ratio 1 part of the former to 14 parts of the latter, thereby producing a liquid containing stable Ag(Pd) nanoparticles, dispersed over the zirconia.

Conclusions (1) The nano-particulate metal dispersions of the invention may be provided with or without a zirconium polymer. Those containing zirconium polymer are particularly suited to the formation of heat resistant products, for example. Dispersions that do not contain zirconium polymer can be used if the presence of zirconium polymer is not required or desired, for example where the presence of zirconium polymer is incompatible with the environment within which the product has to operate.

(2) Although palladium is present in all of the dispersions containing another metal, its content can be less than 10 atomic % of the other metal component if desired.

(3) Mixed metal nano-dispersions can be prepared simply by mixing the individual dispersions to create, for example, a mixed platinum/rhodium/palladium nano-dispersion.

(4) Enhancement of the effectiveness of the metal nanoparticles (for example when applied as a coating to another substrate) can be achieved by associating them with a high surface area component, such as a ceramic sol.

Applications Using Nano-Particulate Dispersions

Example 7

The Creation of a Strongly Bonded Metal Layer on an Epoxy Substrate

In this case the palladium nano-particulate solution (b), described above in Example 4 was applied by spin coating to an epoxy substrate which had an rms surface roughness (Ra) of approximately 1 micron. After drying at 20° C. the specimen was placed in a condensing steam oven for 15 min in order to remove any residual sucrose, followed by heating in air at 105° C. for 15 min. It was then subjected to nickel electroless plating (Rohm and Haas Electronic Materials Niposit® 468). This caused the deposition of a nickel film of approximately 200 nm thickness, which in turn was subjected to electroplating in a standard acid copper bath, resulting in the deposition of a copper layer approximately 30 µm thick. The adhesion of this layer to the substrate was measured by subjecting it to peel testing. This was done by cutting the copper layer into 1 cm wide strips and peeling these perpendicularly to the substrate to remove them. The force required for removal was measured by a load cell. The copper film in this example was found to exhibit peel strengths in excess of 1.0 kgf cm.$^{-1}$ Example 8

The Production of Circuit Boards

The printed circuit board has become a standard device for fixing and interconnecting electronic components. In its most basic form it consists of a sheet of insulating material, such as glass fibre-reinforced epoxy resin, adhesively bonded to a sheet of copper. Additional sheets of epoxy resin and copper can be added to produce a multi-layered structure.

Copper interconnect tracks can be produced by selective etching, as shown in FIG. 1. However this process is associated with two significant disadvantages: (a) undercutting of the copper tracks, which therefore imposes a limit on the line width of the tracks which can be fabricated; and (b) the creation of undesirable copper effluent.

Figure 2:
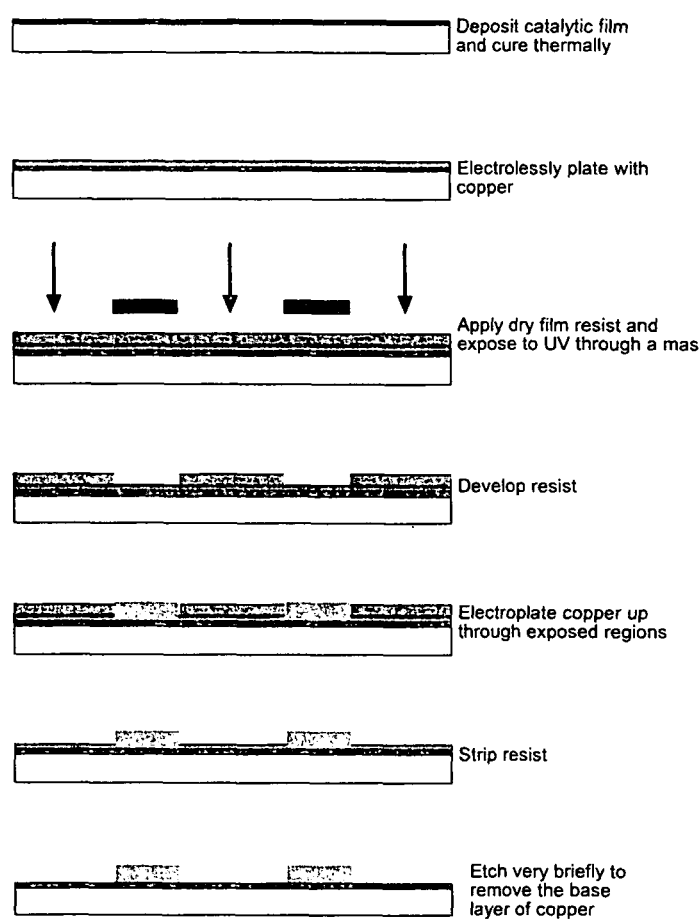
FIG. 2 shows a method of the invention for producing metal tracks.

These problems can be overcome by using another aspect of the current invention. The method is shown schematically in FIG. 2. In this case a coating of the palladium nano-dispersion solution (b), as used in Example 7 above, was applied to an epoxy resin substrate with an rms surface roughness (Ra) of approximately 1 micron. After drying at 20° C. for 5 min., the specimen was placed in a condensing steam oven for 15 min in order to remove any residual sucrose, followed by heating in air at 105° C. for min. It was then subjected to copper electroless plating (Rohm and Haas Electronic Materials Circuposit® 3350 copper plating solution), resulting in the deposition of a copper layer approximately 200 nm in thickness. This was then coated with a UV-sensitive resist, which was patterned by lithography. The exposed copper layer regions were then electroplated with copper, so as to build up a copper metal pattern approximately 30 µm thick. Subsequently the resist was removed, followed by removal, by liquid etching, of the remaining thin layer of copper. In this way high-resolution copper tracks can be created without undercutting; and the production of large volumes of copper effluent is avoided. The process is shown schematically in FIG. 2.

This concept may be extended further by incorporating a catalytic palladium nano-dispersion solution into the near-surface structure of the substrate. In this way the association between the catalyst and the substrate will be even more intimate, thereby enhancing further the degree of bonding between the metal and the substrate.

During the production of multi-layer circuit boards it is necessary to produce vertical interconnects (known as vias) between the horizontal conduction tracks. It has been found that the same palladium nano-particulate-containing solution (b) as used above was suitable for producing such interconnects, in conjunction with copper electroless plating.

Example 9

Silver-Containing Wound Dressings and Other Anti-Bacterial Products

As a simple demonstration of the antibacterial properties of nanodispersed silver, the following experiment was conducted. A piece of linen cloth was coated with a silver nano-dispersion associated with a high surface area zirconia sol, as described above in Example 6. A sample of this cloth (5 cm×3 cm) was placed in fresh whole milk (150 ml) and left unsealed at room temperature. After two weeks the milk had retained its appearance and its characteristic fresh odour, whereas a corresponding sample of fresh milk showed visible separation and exhibited a characteristic sour smell.

Other possible uses for the silver nano-particulate solution include anti-bacterial filters, clothing, ointment and paint.

Example 10

The Use of Metal Nano-Dispersion Liquids in Printing

Example 8 above describes a means of depositing metal in a precise, pre-determined pattern. Another way to achieve this is would be to use nano-particulate metal dispersion liquids as printing ink, and deposit it on to the substrate by either ink-jet printing or by other established ink transfer processes. Naturally in these cases the physical properties of the ink would require to be optimized (for example in terms of its viscosity) so as to meet the requirements of the particular printing process. Having been deposited in this way, the ink can then, if necessary, be subjected to electroless plating (using in this case a palladium nano-particulate dispersion) in order to build up a pattern in an appropriate metal, such as copper, nickel, or silver.

In order to demonstrate the principles of the process in a simple way, a coating of the palladium nano-dispersion (b), as used in Examples 7 and 8 above, was painted on to a patterned rubber stamp, and transferred to the surface of a piece of epoxy resin. After drying at 20° C. in air for 5 min the specimen was placed in a condensing steam oven for 15 min to remove any residual sucrose, followed by heating in air at 105° C. for 15 min. It was then subjected to nickel electroless plating, as described in Example 7 above. This resulted in the production of a patterned film of nickel (approximately 200 nm in thickness) on the surface of the epoxy resin.

The invention claimed is:

1. A process for the production of an aqueous dispersion of metal nano particles comprising palladium, the process comprising: the admixture of a water soluble organic polymer, a palladium salt and a first reducing agent, which is a zirconium nitrate polymer, to an aqueous liquid.

2. A process according to claim 1 wherein the palladium salt is selected from the group consisting of palladium nitrate or palladium chloride.

3. A process according to claim 1 wherein the water soluble organic polymer is selected from the group consisting of polyvinyl alcohol, starch, gelatine and polyvinyl acetate.

4. A process according to claim 1 wherein the metal nano particles comprise palladium and a second metal and the process comprises the additional step of adding a salt of the second metal to the aqueous liquid after formation of the metal nano particles comprising palladium.

5. A process according to claim 4 wherein the second metal is selected from the group consisting of platinum, rhodium, silver, gold and copper.

6. A process according to claim 1 wherein a second reducing agent is added to the aqueous liquid.

7. A process according to claim 6 wherein the second reducing agent is selected from the group consisting of hydrogen gas and water soluble reducing agents.

8. A process according to claim 7 wherein the second reducing agent is ascorbic acid.

9. A process according to claim 1 where sucrose is added to the aqueous liquid as a stabilizing agent for the palladium particles.

10. A process according to claim 1 further comprising the step of associating the metal nanoparticles with a ceramic sol.

11. A process according to claim 10, wherein the ceramic sol is selected from the group consisting of dispersions of zirconia, alumina, silica and titania.

12. The process of claim 1, further comprising applying the aqueous dispersion of metal nano particles to a surface.

13. A mixed metal catalyst prepared by a process comprising the step of mixing at least two aqueous dispersions of metal nano particles comprising palladium; wherein at least one of the said two aqueous dispersions is prepared according to claim 4 and the other is prepared according to claim 4, using a different second metal, or is prepared according to claim 1 and does not include a second metal.

14. An aqueous dispersion of nano particles comprising palladium metal suspended in an aqueous liquid comprising a water soluble polymer and a zirconium nitrate polymer.

15. An aqueous dispersion according to claim 14 wherein the water soluble polymer is selected from the group consisting of polyvinyl alcohol, starch, gelatine and polyvinyl acetate.

16. An aqueous dispersion according to claim 14 further comprising a saccharide as stabilizer.

17. An aqueous dispersion according to claim 14 wherein the nano particles further comprise a second metal.

18. An aqueous dispersion according to claim 17 wherein the second metal is selected from the group consisting of platinum, rhodium, silver, gold and copper.

* * * * *